May 24, 1966 D. BARRY, JR Plant Pat. 2,630
BOUGAINVILLEA PLANT
Filed July 22, 1964
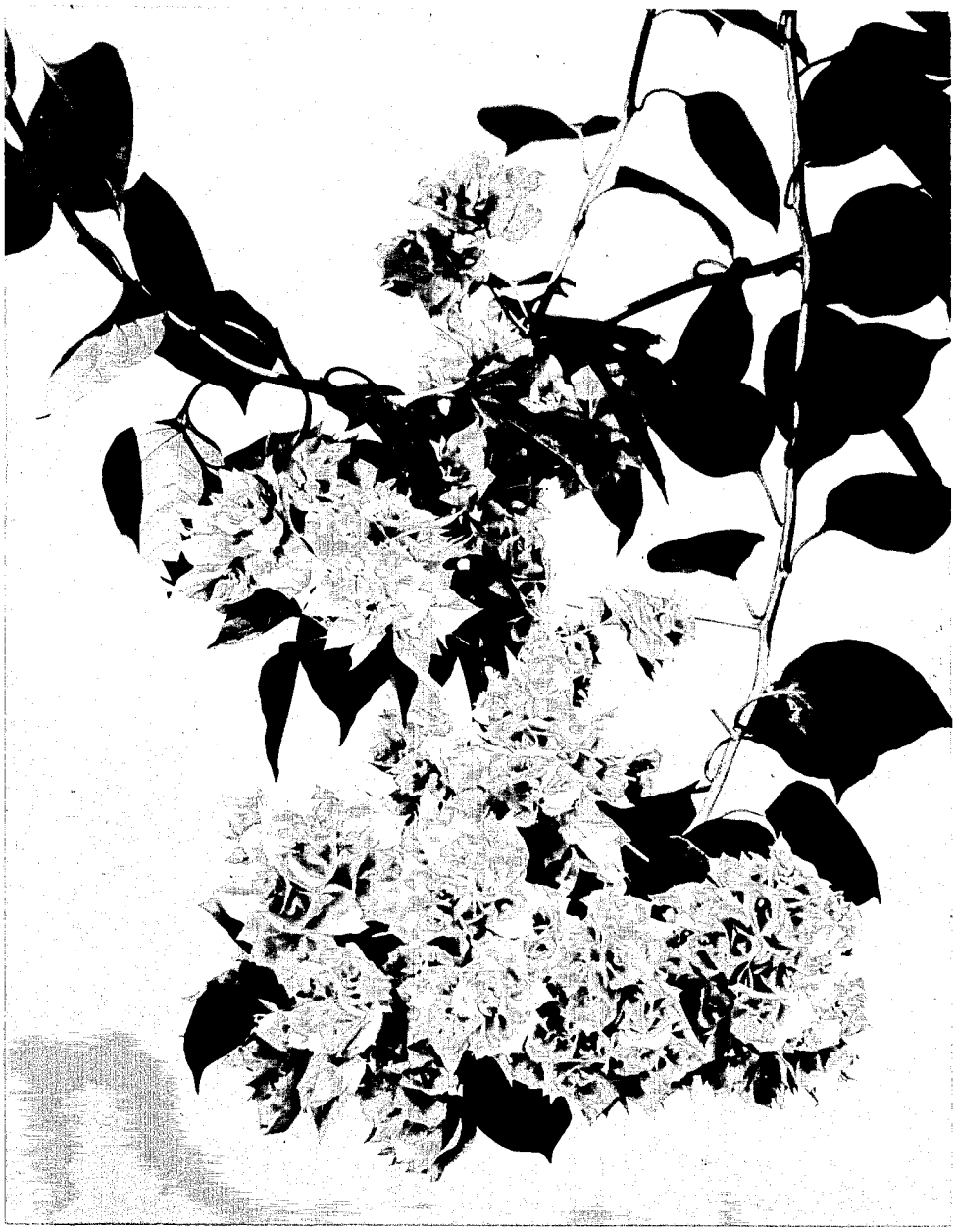
Inventor.
David Barry, Jr.
By: Robb & Robb
Attorneys.

United States Patent Office

Plant Pat. 2,630
Patented May 24, 1966

2,630
BOUGAINVILLEA PLANT

David Barry, Jr., 11977 San Vincente Blvd., Los Angeles, Calif. 90049

Filed July 22, 1964, Ser. No. 384,566
1 Claim. (Cl. Plt.—54)

The present invention relates to a new and distinct variety of bougainvillea plant which was discovered by me as an apparent mutation amongst a group of bougainvillea plants of unknown parentage which were being grown by me in my cultivated commercial nursery gardens located in Los Angeles, California.

Prior to my discovery aforementioned, I obtained from the Philippines a number of rooted cuttings of various unidentified varieties of bougainvillea plants of unknown parentage from which I hoped to develop a stock of commercial plants suitable for propagation and sale in the United States. These original cuttings were in very poor condition when the shipment reached me, as the cuttings had dried out and lost their leaves, and the roots thereof were to all appearances quite dead. However, I succeeded in re-rooting most of the cuttings and I planted them in one of the greenhouses on the premises of my nursery gardens referred to above. All of the plants but one developed into typical bougainvillea plants having the usual three floral bracts common to those varieties native to South America. The exceptional plant aforementioned surprisingly was found to have a double floral structure, with an unusual multiple number of bracts presenting a most distinctive and highly attractive appearance. Continued close observations of this outstanding plant and of progeny thereof asexually reproduced by me therefrom by means of rooted cuttings which I also planted in my gardens referred to in the foregoing, convinced me that they represent a new and distinct variety unlike any other formerly known to me or previously reported or described in published literature, as evidenced by the following unique combination of features which are outstanding in my new mutation:

(1) A very double floral structure having multiple bracts usually ranging from 9 to 12 or more in number; and (2) A distinctive and attractive bract color which may be generally described as a bright rose color corresponding to Spinel Red when young, but changing to Rosolane Purple at maturity, with the immature bracts being somewhat suffused with yellow-green.

Asexual reproduction of my new bougainvillea variety by own-rooted cuttings, as grown by me in my nursery gardens in Los Angeles, California, shows that the aforementioned characteristics and distinctions come true and are established and transmitted through succeeding propagations.

The accompanying drawing shows typical specimens of the floral stems, foliage and inflorescences of my new variety as depicted in color as nearly true as it is reasonably possible to make the same in a color illustration of this character.

The following is a detailed description of my new bougainvillea variety, with color terminology in accordance with Ridgway's Color Standards and Nomenclature, except where general color terms of ordinary dictionary significance are obvious:

Parentage: A mutation of unkonwn parentage.
Location where grown and observed: Los Angeles, California.

*Plant*

Growth:
*Habit.*—Upright-spreading; semi-scandent.

*New stems.*—1–2 mm. in diameter; lightly tawny-pubescent; glabrescent at maturity. Color—Biscay Green, Plate XVII, or suffused with Purple characteristic of the inflorescence.
*Older stems.*—Glabrous; longitudinally fissured; grooves ½ to 1 mm. wide and spaced 1 to 2 mm. apart. Color—Epidermis Natal Brown, Plate XL with grooves Vinaceous Buff, Plate XL.
*Mature branches.*—Corky. Color—avellaneous to Wood-Brown, Plate XL.
*Spines.*—Infrequent; 6–8 mm. long.

Leaves:
*Internodes.*—About 2 cm. in length, except at base of branches; leaves alternate.
*Texture.*—From thin to subcoriaceous; appressed; puberulent when young; glabrate at maturity except on and near veins.
*Size.*—Lamina (excluding leaves at base of branches): Long—from 2 to 6.5 cm. (average 5.3 cm.); wide—from 1.7 to 5.3 cm. (average 4.1 cm.).
*Petiole.*—From 1.5 to 2.2 cm. long; terete; glabrescent.
*Shape.*—From ovate to subcordate; base obtuse; apex acuminate; margins entire.
*Upper surface.*—Dull; major veins depressed. Color—near Chromium Green, Plate XXXII.
*Lower surface.*—Dull. Color—Biscay Green, Plate XVII. Major veins—raised above surface and being clear Dull Green-Yellow, Plate XVII. Minor veins—evident and being Bice Green, Plate XVII.

*Inflorescence*

Position and abundance: Inflorescences 2 to 5 (average 4) per flowering branch; subterminal on branch; axillary.
Habit: Each inflorescence branch indeterminate, paniculately compound and branching racemose; bracts closely clustered.
Axes: Inflorescence axes terete; from ½ to 1 mm. in diameter. Color—Bordeaux, Plate XII, suffused with green where shaded on plant.
Bracts:
*Arrangement.*—Mostly alternate; occasionally alternately clustered at ends of inflorescence branchlets, giving the entire inflorescence a tufted appearance.
*Number.*—Normally from 9 to 12 or more.
*Habit.*—Sessile, but with one or more strongly decurrent bracts on each inflorescence branchlet; usually the decurrent bract is at the base of each branchlet.
*Size.*—Larger bracts up to 3.8 cm. long and 2.9 cm. wide; bracts grade in size down to minute, since cessation of growth of inflorescence branchlets occurs prior to maturation of all bracts.
*Shape.*—From ovate to subelliptical; base (if not decurrent) acute or obtuse; apex usually accuminate some acute).
*Texture.*—Chartaceous; veins evident; only midvein raised above surface prominently.
*Vesture.*—Finely puberulent when young; pubescent along veins at maturity.
*Color.*—Young bracts Spinel Red, Plate XXVI, changing to Rosolane Purple, Plate XXVI at maturity; both colors are present in all inflorescences, because cessation of growth occurs before all bracts are matured; immature bracts are somewhat suffused with yellow-green because of their denser vesture; midvein and portions of lateral veins Absinthe Green, Plate XXXI.
Flowers: Absent; instead of producing a limited number of bracts, each capable of bearing an epibracteate flower, as is typical for regular bouganvillea varieties, this plant now bears unlimited numbers of sterile bracts.

I claim:

A new and distinct variety of bougainvillea plant, substantially as herein shown and described, characterized particularly as to novelty by the unique combination of a very double floral structure having multiple bracts usually ranging from 9 to 12 or more in number, and a distinctive and attractive bract color which may be generally described as a bright rose color corresponding to Spinel Red when young, but changing to Rosolane Purple at maturity, with the immature bracts being somewhat suffused with yellow-green.

References Cited by the Examiner

UNITED STATES PATENTS

P.P. 2,514 5/1965 Green ---------- Plants 54

ABRAHAM G. STONE, *Primary Examiner.*

T. GRAHAM CRAVER, *Examiner.*

R. E. BAGWILL, *Assistant Examiner.*